(12) United States Patent
Okada

(10) Patent No.: US 8,382,660 B2
(45) Date of Patent: Feb. 26, 2013

(54) ENDOSCOPE SYSTEM HAVING AN ENDOSCOPE AND A TISSUE-COLLECTING APPARATUS

(75) Inventor: Tsutomu Okada, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 923 days.

(21) Appl. No.: 12/047,621

(22) Filed: Mar. 13, 2008

(65) Prior Publication Data

US 2009/0234192 A1   Sep. 17, 2009

(51) Int. Cl.
*A61B 1/00* (2006.01)
*A61B 1/12* (2006.01)
*A61M 1/00* (2006.01)
*B01D 21/00* (2006.01)

(52) U.S. Cl. ........ 600/156; 600/154; 600/158; 604/317; 604/319; 422/527

(58) Field of Classification Search ............... 600/104, 600/153–159, 562–574; 604/317–326, 540–544; 422/527, 534; 423/92; 606/113–115
See application file for complete search history.

(56) References Cited

U.S. PATENT DOCUMENTS

| | | | | |
|---|---|---|---|---|
| 4,870,975 A * | 10/1989 | Cronk et al. | | 600/562 |
| 4,957,492 A * | 9/1990 | McVay | | 604/319 |
| 5,035,688 A * | 7/1991 | Inui | | 604/190 |
| 5,363,860 A * | 11/1994 | Nakao et al. | | 600/573 |
| 5,575,293 A * | 11/1996 | Miller et al. | | 600/565 |
| 5,624,418 A * | 4/1997 | Shepard | | 604/319 |
| 5,797,742 A * | 8/1998 | Fraker | | 433/92 |
| 5,971,917 A * | 10/1999 | Komi et al. | | 600/159 |
| 6,110,127 A * | 8/2000 | Suzuki | | 600/565 |
| 6,142,956 A * | 11/2000 | Kortenbach et al. | | 600/564 |
| 6,389,609 B1 * | 5/2002 | Andritz | | 4/144.1 |
| 6,428,316 B1 * | 8/2002 | Rodriquez | | 433/92 |
| 7,244,236 B2 * | 7/2007 | Merkle | | 600/575 |
| 8,070,756 B2 * | 12/2011 | Secrest et al. | | 606/113 |

(Continued)

FOREIGN PATENT DOCUMENTS

EP   1 813 184 A1   8/2007
JP   S62-74804   5/1987

(Continued)

*Primary Examiner* — Matthew J Kasztejna
*Assistant Examiner* — Ryan Henderson
(74) *Attorney, Agent, or Firm* — Scully Scott Murphy & Presser, PC

(57) ABSTRACT

An endoscope system includes: an endoscope having an insertion section extending from an operation section operated by an operator into a human body, and an operation channel having a first end section having an opening at a distal end of the insertion section and a second end section passing through the insertion section and having an opening at the operation section; a tissue-collecting apparatus connected to a connecting pipeway branching from a branch section formed to the second end section in the operation channel, and capable of seizing tissue retracted into the operation channel; an aspirator for producing suction force for suctioning the tissue into the operation channel; and a suction pipeway connecting the tissue-collecting apparatus to the aspirator. The tissue-collecting apparatus has: a tissue-collecting case having a first chamber connected to the connecting pipeway, a second chamber connected to the suction pipeway, and a communication path provided to lateral walls of the first chamber and the second chamber and causing the first chamber to communicate with the second chamber; and a tissue-collecting filter detachably enclosed in the first chamber.

4 Claims, 12 Drawing Sheets

| U.S. PATENT DOCUMENTS | | | |
|---|---|---|---|
| 8,088,079 B2 * | 1/2012 | Kaye et al. | 600/562 |
| 2004/0068291 A1 * | 4/2004 | Suzuki | 606/205 |
| 2006/0287579 A1 * | 12/2006 | Okada | 600/156 |
| 2007/0179341 A1 | 8/2007 | Okada | |
| 2007/0191731 A1 | 8/2007 | Kaye et al. | |

| FOREIGN PATENT DOCUMENTS | | | |
|---|---|---|---|
| JP | H11-267089 | | 10/1999 |
| JP | 2006346179 A | * | 12/2006 |
| JP | 2007-202630 | | 8/2007 |

* cited by examiner

ENDOSCOPE SYSTEM HAVING AN ENDOSCOPE AND A TISSUE-COLLECTING APPARATUS

BACKGROUND OF THE INVENTION

1. Field of the Invention

The present invention relates to an endoscope system for endoscopic treatment use capable of collecting tissue obtained from a living body.

2. Background Art

In some conventional endoscopic methods for collecting a seized tissue of a living body used in various manipulations using an endoscope, tissue incised with a procedure instrument is suctioned by using a channel of an endoscope. Japanese Unexamined Utility Model (Registration) Application Publication No. S62-74804 discloses an example of a configuration including a cap capable of sealing a chamber formed at a forceps port of a forceps channel of an endoscope; and a tissue collection basket trap disposed in the chamber. A pipe serving as a forceps channel and a suction pipeway compatibly is inserted into the basket, and a pipe connected to an aspirating apparatus is disposed in the exterior of the basket. Tissue incised or the like from a human body upon actuating the aspirating apparatus is introduced into the basket through the pipe. The basket having a shape that allows passage of fluid but not the passage of tissue seizes the incised tissue alone.

Japanese Unexamined Patent Application, First Publication No. H11-267089 discloses an example of a configuration in which a suction tube having a valve and a collection trap provided at some midpoint thereof and extracted from a proximal end section of a forceps channel of an endoscope into the exterior of the endoscope is connected to an aspirating apparatus. An incision forceps passed through the forceps channel upon incising a tissue, e.g., polyp is extracted from the forceps channel, and a forceps port is closed by a forceps cap. Opening the valve subsequently causes a suction force of the aspirating apparatus to act on the forceps channel through the suction tube, thereby suctioning the incised tissue. The tissue upon entering the suction tube from the forceps channel and getting out of the endoscope is collected by the collection trap.

However, in the configuration disclosed by Japanese Unexamined Utility Model (Registration) Application Publication No. S62-74804, the collection trap formed in the forceps channel for inserting the procedure instrument therethrough prevents insertion of the basket inevitably if the procedure instrument has been inserted without having the basket. Sometimes, this case loses track of the incised tissue while attaching the basket since the incised tissue cannot be collected immediately. Another drawback of the configuration for inserting the basket into the forceps channel is unsatisfactory operability in insertion and retraction of the procedure instrument relative to the forceps channel.

Also, an operator encounter unsatisfactory operability in the configuration disclosed by Japanese Unexamined Patent Application, First Publication No. H11-267089 including a collection trap disposed at a considerable distance from the forceps channel, and separately extending three pipeways including an endoscope insertion section extending from the endoscope operation section grasped by the operator into the human body; a universal code extending to a control unit; and a suction tube for tissue collection. Another drawback in this configuration is that the operator while operating the endoscope has difficulty in removing a collected tissue from the collection trap, or attaching and detaching a filter for tissue collection since the endoscope is disposed at a considerable distance from the endoscope.

In an attempt to solve drawbacks of the aforementioned configurations, Japanese Unexamined Patent Application, First Publication No. 2007-202630 discloses a configuration of a tissue-collecting apparatus having a tissue-collecting case and a tissue-collecting filter detachably attached to the tissue-collecting case that are disposed between a connecting pipeway and a suction pipeway that branch from a branch section provided to the proximal end of an operation channel (forceps channel) passing in the endoscope. In this configuration, the endoscope has the tissue-collecting apparatus attached thereto; therefore, a pipeway connecting the endoscope with the tissue-collecting apparatus is not arranged at the exterior of the endoscope.

The tissue-collecting apparatus collects an incised tissue from the distal end of the endoscope insertion section through the branch section. The tissue-collecting apparatus disposed to the operation channel proximally relative to the branch section prevents the procedure instrument from interfering with the tissue-collecting apparatus.

However, sometimes drainage remains in the tissue-collecting case partly upon seizing a tissue with a tissue-collecting filter and stopping an aspirating apparatus in the configuration disclosed by Japanese Unexamined Patent Application, First Publication No. 2007-202360. FIG. 23 shows a tissue-collecting case 111 of a tissue-collecting apparatus 110 provided to an endoscope operation section 100 disposed in a tilting state relative to the endoscope operation section 100. In this case, detaching a tissue-collecting filter 112 from a tissue-collecting case 111 for taking out the seized tissue causes the drainage remaining in the tissue-collecting case 111 to possibly spill therefrom.

In another case, the tissue-collecting case 111 of the tissue-collecting apparatus 110 is disposed substantially parallel with the endoscope operation section 100 as shown in FIG. 24. Tilting the endoscope operation section 100 and continuing the operation of an endoscope while the tissue-collecting filter 112 is detached from the tissue-collecting case 111 sometimes causes drainage D remaining in the tissue-collecting case 111 to spill therefrom, thereby soiling the operator and the area therearound.

SUMMARY OF THE INVENTION

The present invention was conceived in consideration of the aforementioned circumstances, and an object thereof is to provide a leak-resistant drainage structure to an endoscope system including a tissue-collecting apparatus for collecting tissue, or to prevent drainage from leaking. A first aspect of the present invention is an endoscope system which includes: an endoscope having an insertion section extending from an operation section operated by an operator into a human body, and an operation channel having a first end section having an opening at a distal end of the insertion section and a second end section passing through the insertion section and having an opening at the operation section; a tissue-collecting apparatus connected to a connecting pipeway branching from a branch section formed to the second end section in the operation channel, and capable of seizing tissue retracted into the operation channel; an aspirator for producing suction force for suctioning the tissue into the operation channel; and a suction pipeway connecting the tissue-collecting apparatus to the aspirator. The tissue-collecting apparatus has: a tissue-collecting case having a first chamber connected to the connecting pipeway, a second chamber connected to the suction pipeway, and a communication path provided to lateral walls of the first chamber and the second chamber and causing the first chamber to communicate with the second chamber; and a tissue-collecting filter detachably enclosed in the first chamber.

PREFERRED EMBODIMENTS

An endoscope system according to a first embodiment of the present invention will be explained as follows with reference to FIGS. 1 to 13.

Figure 1:
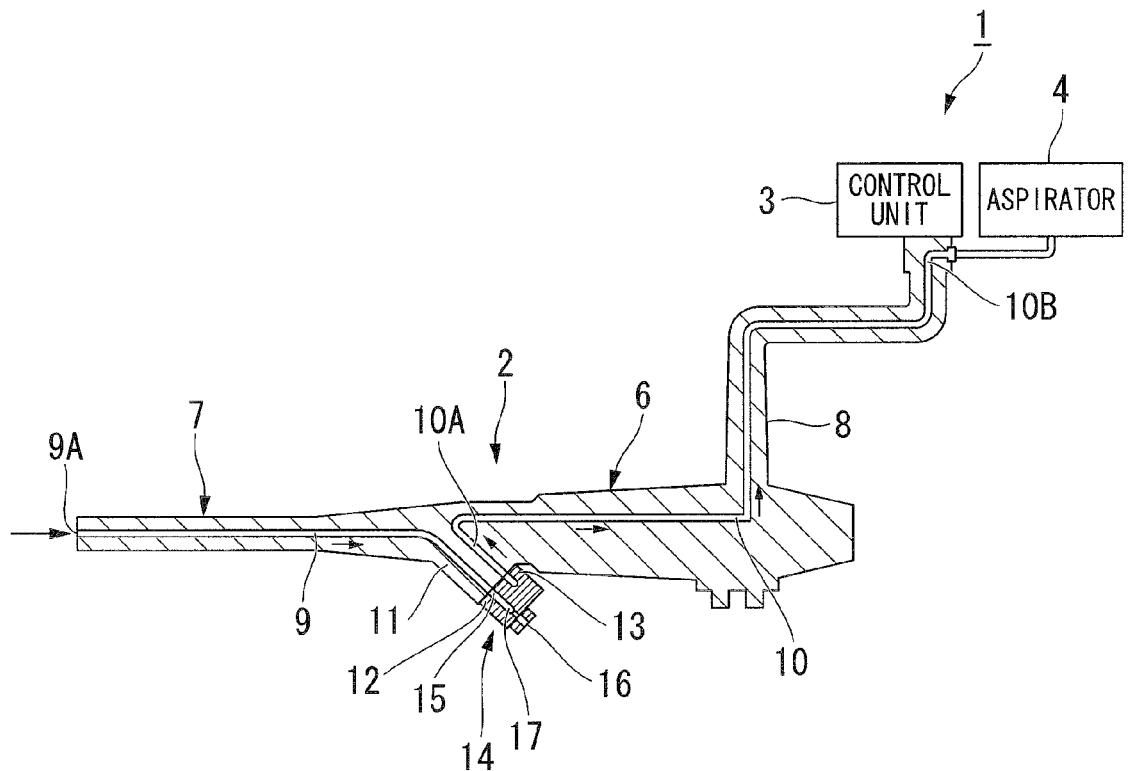
FIG. 1 is a general view of a structure of the endoscope system according to a first embodiment of the present invention.
Figure 2:
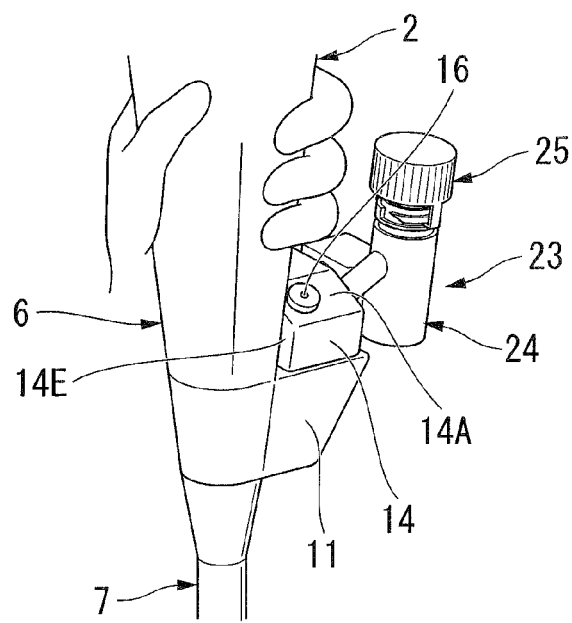
FIG. 2 shows an endoscope operation section of the endoscope system and therearound.

FIG. 1 shows the configuration of an endoscope system 1 according to the present embodiment. FIG. 2 shows an operation section 6 of an endoscope of the endoscope system 1 and therearound. As shown in FIGS. 1 and 2, the endoscope system 1 is provided with: an endoscope 2; a control unit 3; an aspirator 4; an attachment 14 detachably attached to the endoscope 2; and a tissue-collecting apparatus 23 fixed to the endoscope 2 via the attachment 14.

The endoscope 2 has the operation section 6 operated by the operator; and a flexible and elongated insertion section 7 extending from the distal end of the operation section 6. The operation section 6 connected to the control unit 3 via a universal cable 8 has an angle knob and various buttons and switches disposed thereon. An operation channel 9 and a suction pipeway 10 are formed in the endoscope 2.

The operation channel 9 having a distal-end-opening section 9A disposed at the distal end section of the insertion section 7 extends to a lateral section 11 of the operation section 6. A proximal end connection port of the operation channel 9 protruding from the lateral section 11 forms a second connection section 12. The lateral section 11 has an opening of the distal end section 10A of the suction pipeway 10. This opening is formed close to a second connection section 13 protruding from the lateral section 11.

A proximal end section 10B of the suction pipeway 10 extending from the operation section 6 and passing through the universal cable 8 is connected to the aspirator 4. The second connection section 12 and the second connection section 13 protrude substantially in parallel with each other from the lateral section 11. The attachment 14 is attached to each connection section 12 and 13.

The attachment 14 is formed by a material having a low degree of hardness and a low degree of strength relative to the main body of the endoscope 2, e.g., resin, or elastic material, etc.

Figure 3:
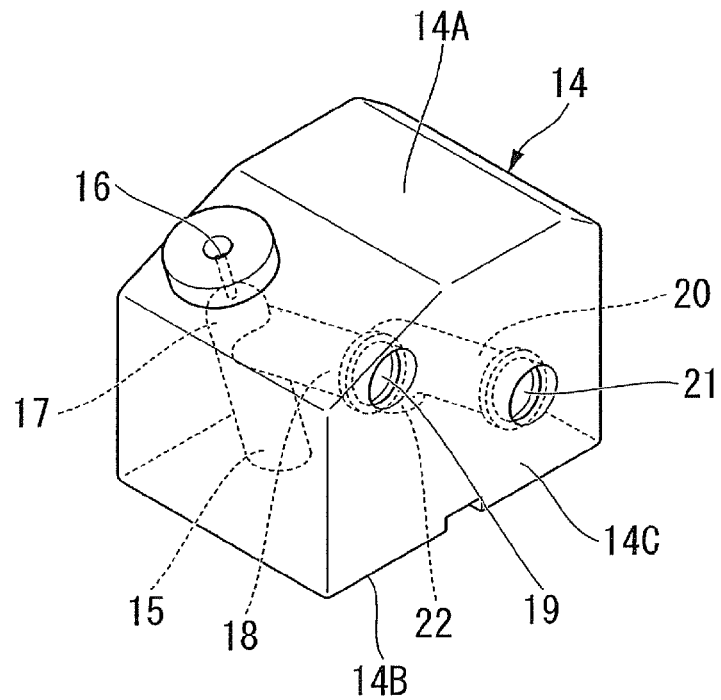
FIG. 3 is a perspective view of an attachment of the endoscope system.
Figure 4:
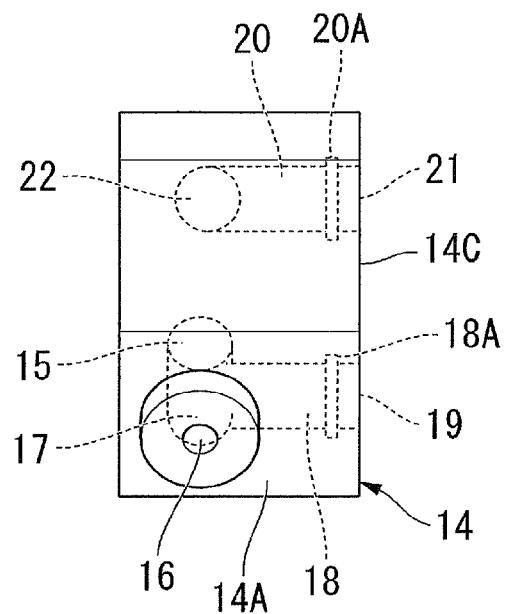
FIG. 4 is a plan view of the attachment.

FIG. 3 is a perspective view of the attachment 14. FIG. 4 is a plan view of the attachment 14. As shown in FIGS. 3 and 4, the first connection pipeway 15 connecting to the operation channel 9 unitarily penetrates from an upper surface 14A to a lower surface 14B of the attachment 14.

The second connection section 12 can engage with the first connection pipeway 15 at the lower surface 14B. An instrument-insertion inlet 16 is formed on the upper surface 14A of the first connection pipeway 15. Furthermore, a branch section 17 is formed in the first connection pipeway 15, and a first connection pipeway 18 extends therefrom. An opening of the first connection pipeway 18 formed on a lateral surface 14C of the attachment 14 becomes a distal-end-connecting port 19.

A second connection pipeway 20 extending substantially parallel with the first connection pipeway 18 is provided to the attachment 14. An end section of the second connection pipeway 20 has a proximal end connection port 21 formed on the lateral surface 14C of the attachment 14. The other end section is connected to a second-coupling pipeway 22 in the attachment 14. The second-coupling pipeway 22 has an opening section on only a lateral surface 14C of the attachment 14. The opening section has a shape allowing the second connection section 13 connected to the suction pipeway 10 of the endoscope 2 to engage therewith.

As shown in FIG. 2, the tissue-collecting apparatus 23 is detachably attached to the distal-end-connecting port 19 and the proximal end connection port 21 of the attachment 14.

Figure 5:
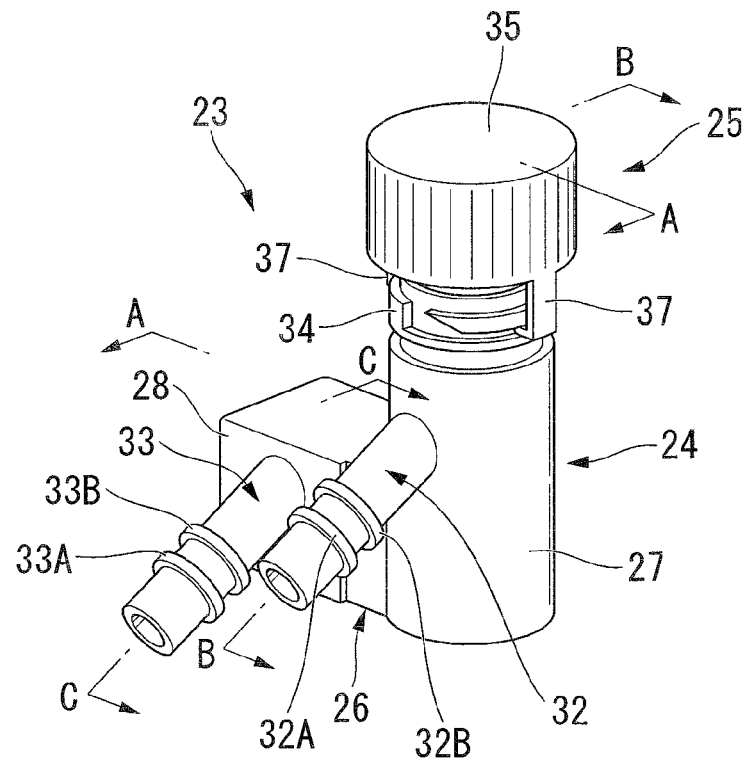
FIG. 5 is a perspective view of a tissue-collecting apparatus of the endoscope system.
Figure 6:
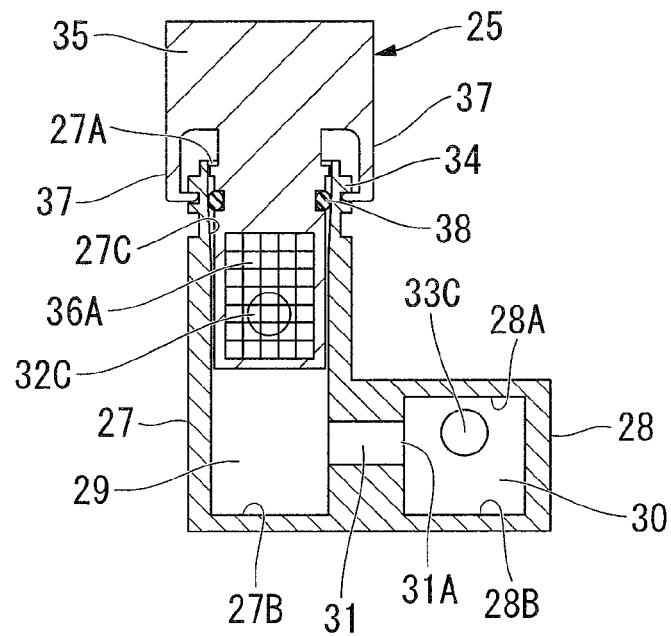
FIG. 6 is a cross-sectional view taken along the line A-A in FIG. 5.
Figure 7:
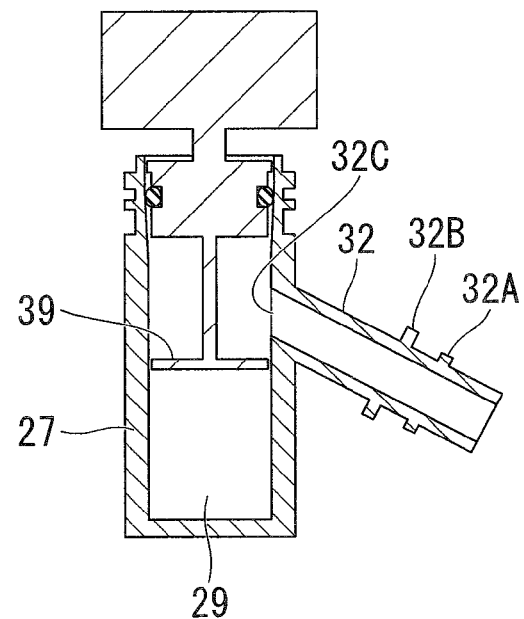
FIG. 7 is a cross-sectional view taken along the line B-B in FIG. 5.
Figure 8:
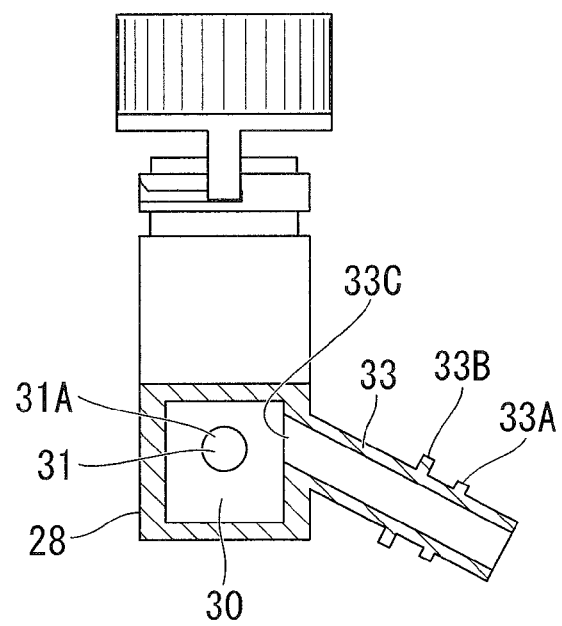
FIG. 8 is a cross-sectional view taken along the line C-C in FIG. 5.

FIG. 5 is a top plan view of the attachment 14. FIGS. 6 to 8 are cross-sectional views taken along the line A-A, the line B-B, and the line C-C of FIG. 5 respectively. As shown in FIGS. 5 and 6, the tissue-collecting apparatus 23 has a tissue-collecting case 24 and a tissue-collecting filter 25 detachably attached to the tissue-collecting case 24. The tissue-collecting case 24 has a casing main unit 26 made of a see-through material, e.g., resin or glass enabling visual observation thereinside.

The casing main unit 26 is formed by a first main body 27 and a second main body 28 connected to the first main body 27. As shown in FIG. 6, the casing main unit 26 has a first chamber 29 and a second chamber 30 formed thereinside. The first chamber 29 is a space defined by an opening section 27A and a bottom section 27B of the first main body 27. The second chamber 30 is a space defined by a ceiling section 28A and a second rotation mechanism of the second main body 28. The bottom section 27B of the first chamber 29 is substantially flush with the bottom section 28B of the second chamber 30. The first chamber 29 communicates with the second chamber 30 via a communication path 31 having an opening at each wall surface of the chamber. An opening section 31A of the communication path 31 formed to the second chamber 30 is disposed above the bottom section 28B of the second chamber 30 by a predetermined distance.

A distal-end-pipeway 32 and a proximal end pipeway 33 extend parallel with each other from a lateral section of the first rotation mechanisms 1351A and 1351B and a lateral section of the operation unit respectively as shown in FIG. 5 diagonally relative to the casing main unit 26. An annular protrusion 32A and an annular protrusion 32B are formed on the outer periphery of the distal-end-pipeway 32. The annular protrusion 32B having a diameter greater than that of the annular protrusion 32A is disposed in the vicinity of the casing main unit 26 relative to the annular protrusion 32A. An annular protrusion 33A and an annular protrusion 33B are formed on the outer periphery of the proximal end pipeway 33 similarly to the distal-end-pipeway 32. The annular protrusion 33B has a diameter greater than that of the annular protrusion 33A. The pipeways 32 and 33 communicate with the first chamber 29 and the second chamber 30 at a first communication port 32C and a second communication port 33C respectively.

As shown in FIG. 6, the first main body 27 has a circular opening section 27A. A pair of filter engagement sections 34 are provided to the outer periphery of the opening section 27A. A taper surface 27C having an inner diameter reducing toward the bottom section 27B is formed to the opening section 27A of the first main body 27.

Figure 9:
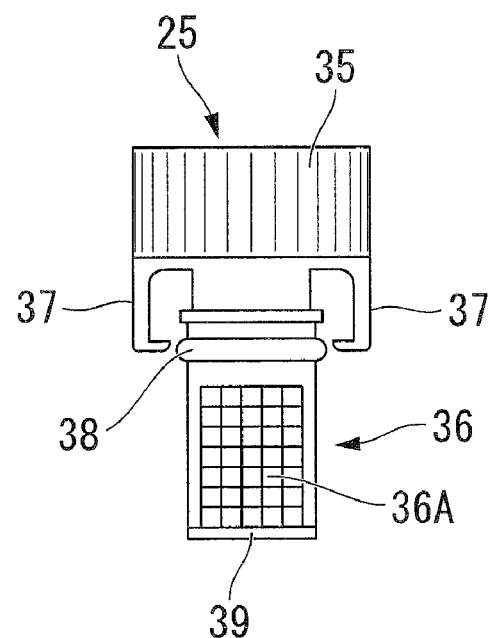
FIG. 9 shows a tissue-collecting filter of the endoscope system.
Figure 11A:
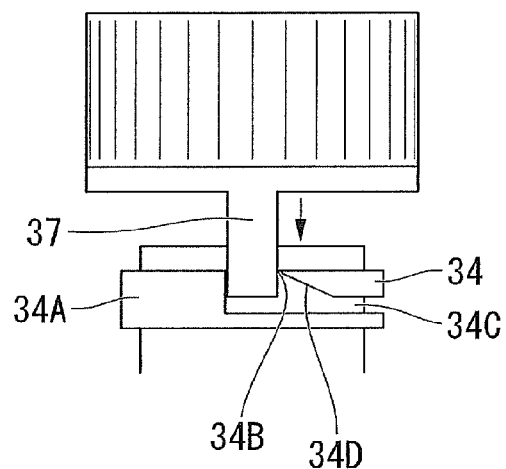
FIGS. 11A and 11B illustrate movement of attaching the tissue-collecting filter to the tissue-collecting apparatus.
Figure 11B:
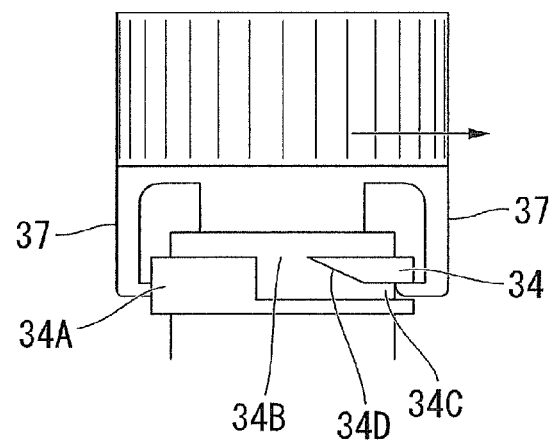

As shown in FIGS. 5, 6, and 9, the tissue-collecting filter 25 has a lid section 35 and a filter section 36 extending from the lid section 35 and freely entering the opening section 27A of the first main body 27. A pair of fixture sections 37 are provided to the lid section 35. The fixture sections 37 can engage with the filter engagement section 34 of the first main body 27. As shown in FIG. 11A, a pair of filter engagement sections 34 each have a pair of taper sections 34D. A pair of protrusion sections 34A are provided to face each other in a radial direction with respect to the circumference of the lid section 35 in plan view. In addition, a pair of insertion ports 34B, and a pair of engagement sections 34C are provided similarly. The taper sections 34D are slopes for connecting the insertion port to the engagement section 34C. Rotating the fixture sections 37 of the tissue-collecting filter 25 upon inserting the fixture section 37 into the insertion port 34B causes the fixture sections 37 to move along the taper section 34D, thereby causing the fixture sections 37 to be inserted into the engagement section 34C.

The fixture sections 37 moving along the taper section 34D causes a seal O ring 38 attached to a lower part of the lid section 35 as shown in FIG. 6 to be crushed by the taper surface 27C, thereby sealing the opening section 27A of the first main body 27.

The porous mesh filter section 36 allows fluid to pass therethrough but not tissue. Two tissue-seizing surfaces 36A assembled in one unit are provided to a front side and a back side of the filter section 36. The tissue-seizing surfaces 36A are disposed in substantially parallel relative to a line segment joining the pair of fixture sections 37.

Therefore, engaging the fixture sections 37 with the filter engagement section 34 of the first main body 27 causes either tissue-seizing surface 36A to be disposed to face the first communication port 32C regularly, thereby, enabling the attachment of the tissue-collecting filter 25 without considering its direction. The clearance between the filter section 36 and the first main body 27 is set to prevent tissue from passing therethrough.

Figure 10:
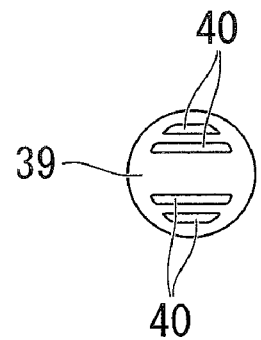
FIG. 10 shows a plate of the tissue-collecting filter.

As shown in FIGS. 7 and 9, a plate 39 is provided to the tip of the filter section 36. The plate 39 does not reduce suction force since a slit 40 is provided to the plate 39 as shown in FIG. 10.

Figure 12:
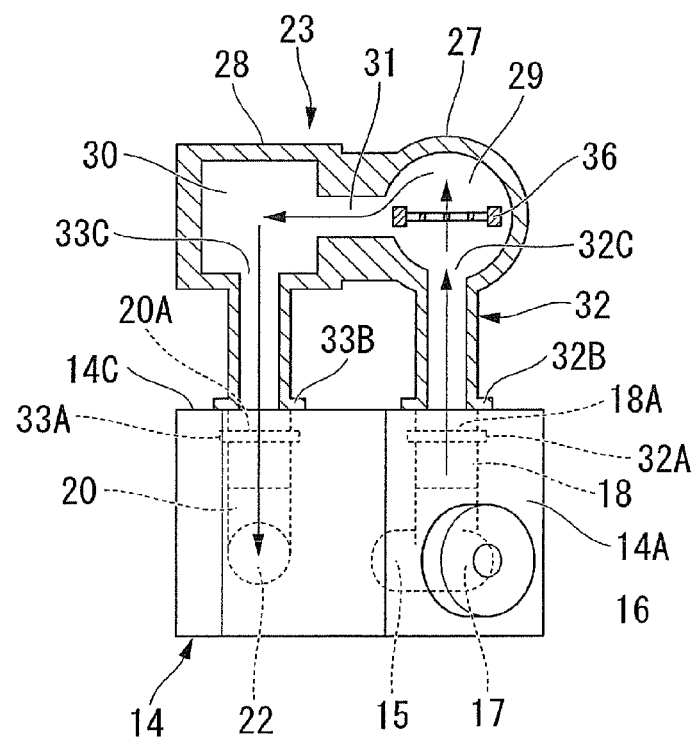
FIG. 12 shows the tissue-collecting apparatus attached to the attachment partly in cross-sectional view.

As shown in FIG. 12, attaching the tissue-collecting apparatus 23 to the attachment 14 causes the distal-end-pipeway 32 to be inserted into the first connection pipeway 18. The annular protrusion 32A is locked at an annular groove 18A of the first connection pipeway 18, and the annular protrusion 32B abuts the lateral surface 14C. This results in causing the first connection pipeway 15 to communicate with the first chamber 29 of the first main body 27 of the tissue-collecting apparatus 23. The filter section 36 of the tissue-collecting filter 25 is inserted into the first chamber 29.

Similarly, inserting the proximal end pipeway 33 into the second connection pipeway 20 causes the annular protrusion 33A to be locked at an annular groove 20A, and causes the annular protrusion 33B to abut the lateral surface 14C. This results in causing the second-coupling pipeway 22 to communicate with the second chamber 30 of the second main body 28 of the tissue-collecting apparatus 23.

The operation in the present embodiment will be explained.

To start with, an operator attaches the tissue-collecting apparatus 23 to the attachment 14 as shown in FIG. 12. Subsequently, the second connection section 12 and the second connection section 13 of the operation section 6 are fit into the first connection pipeway 15 and the second-coupling pipeway 22 of the attachment 14 respectively, and then the attachment 14 is fixed to the endoscope 2.

This state of attachment 14 is attached to the endoscope 2 so that a lateral surface 14E (first surface) is disposed toward the operation section 6 as shown in FIG. 2. This results in disposing the tissue-collecting apparatus 23 attached in the vicinity of the lateral surface 14C (second surface) to be opposite the operation section 6 relative to the attachment 14.

The insertion section 7 in this state is inserted into a patient's body, and a procedure instrument (e.g., incision forceps), not shown in the drawing, is inserted into the instrument-insertion inlet 16 of the attachment 14. The procedure instrument upon entering the first connection pipeway 15 of the attachment 14 and the operation channel 9 in the endoscope 2 projects from the distal end section of the insertion section 7. The procedure instrument upon incising a target site tissue is removed from the endoscope 2 and the attachment 14. The instrument-insertion inlet 16 closing with its restoring force seals the opening thereof.

Suctioning the incised tissue necessitates actuating the aspirator 4. The produced suction force acts on the tissue upon passing through the suction pipeway 10 (including the second-coupling pipeway 22 and the second connection pipeway 20 of the attachment 14), the tissue-collecting apparatus 23, the first connection pipeway 18, and the operation channel 9 (including the first connection pipeway 15). Upon passing through the operation channel 9, branch section 17, and the first connection pipeway 18, the incised tissue, not shown in the drawing, and nearby fluid are suctioned into the first chamber 29 of the first main body 27 of the tissue-collecting apparatus 23. The tissue is seized by the tissue-seizing surface 36A of the filter section 36 in the first chamber 29. The fluid, upon passing through the mesh tissue-seizing surface 36A, the slit 40 of the plate 39, the communication path 31, the first chamber 29, the second chamber 30, the attachment 14, and the suction pipeway 10, is drained from the aspirator 4.

Figure 13A:
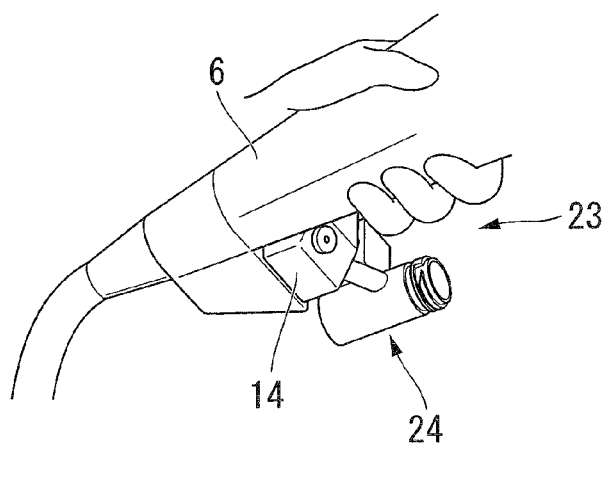
FIG. 13A shows the movement of the endoscope system in use.
Figure 13B:
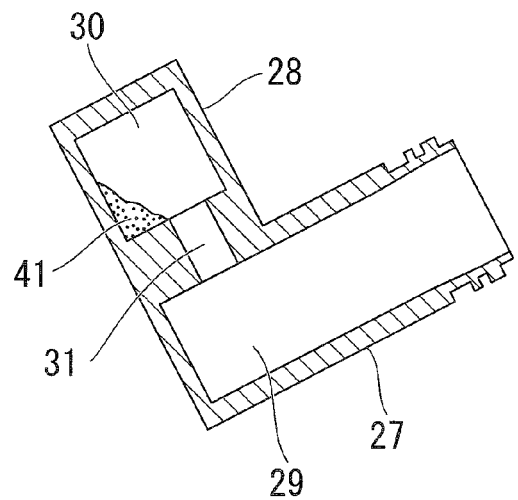
FIG. 13B shows a casing main unit of the tissue-collecting apparatus during the movement shown in FIG. 13A.

The operator upon seizing the tissue stops the aspirator 4. The tissue-collecting filter 25 is detached from the tissue-collecting case 24, and then the tissue is collected. Stopping the aspirator 4 sometimes causes backflow of a part of the fluid remaining in the suction pipeway 10 back into the tissue-collecting case 24. Fluid 41 flowing back to the second chamber 30 and remaining there hardly moves from the second chamber 30 to the first chamber 29 as shown in FIG. 13B if the operation section 6 is tilted as shown in FIG. 13A. Therefore, the fluid 41 does not spill out, and does not soil the operator and therearound.

The endoscope system 1 according to the present embodiment causes the fluid 41 to not be fully suctioned with the incised tissue and remain in the second chamber 30 of the tissue-collecting case 24 to resist moving to the first chamber 29, since the first chamber 29 and the second chamber 30 are formed in the tissue-collecting case 24 and since the communication path 31 having openings on the lateral walls of the two chambers joins the two chambers above the bottom sections of the first chamber 29 and the second chamber 30. An aspirator 4 is stopped upon seizing the incised tissue by the tissue-collecting filter 25, and then, the tissue-collecting filter 25 is detached from the tissue-collecting case 24 for taking out the seized tissue. Tilting the operation section 6 while continuing this state of endoscope 2 hardly causes the fluid 41 remaining in the second chamber 30 of the tissue-collecting case 24 to spill out of the tissue-collecting case 24, thereby providing clean operation to the operator and therearound.

Second Embodiment

A second embodiment of the present invention will be explained with reference to FIGS. 14 to 18.

Figure 14:
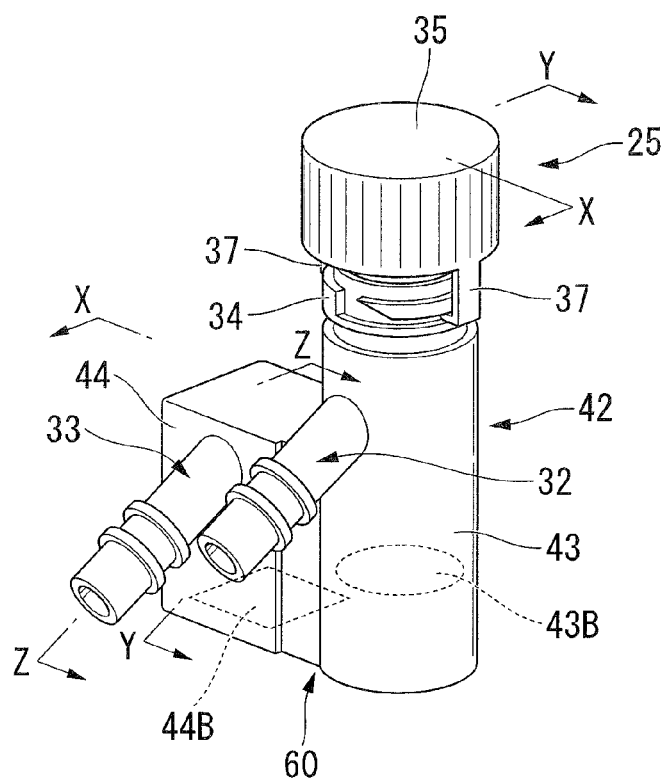
FIG. 14 is a perspective view of a tissue-collecting case of an endoscope system according to a second embodiment of the present invention.
Figure 15:
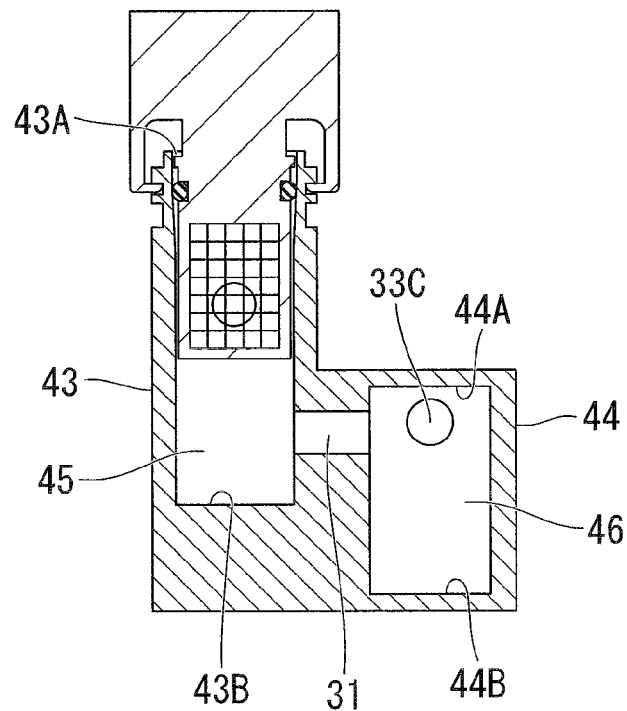
FIG. 15 is a cross-sectional view taken along the line X-X in FIG. 14.
Figure 16:
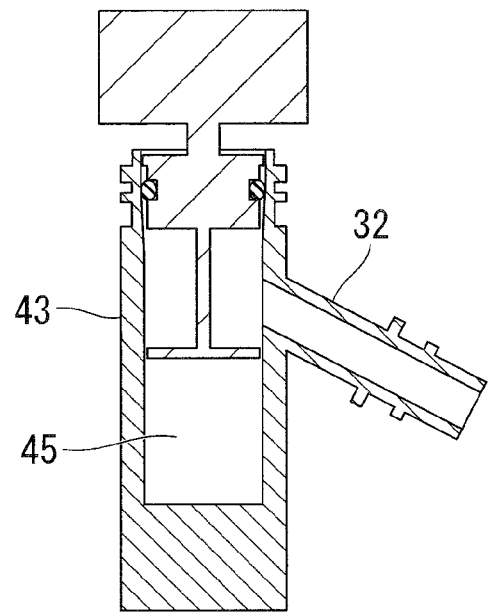
FIG. 16 is a cross-sectional view taken along the line Y-Y in FIG. 14.
Figure 17:
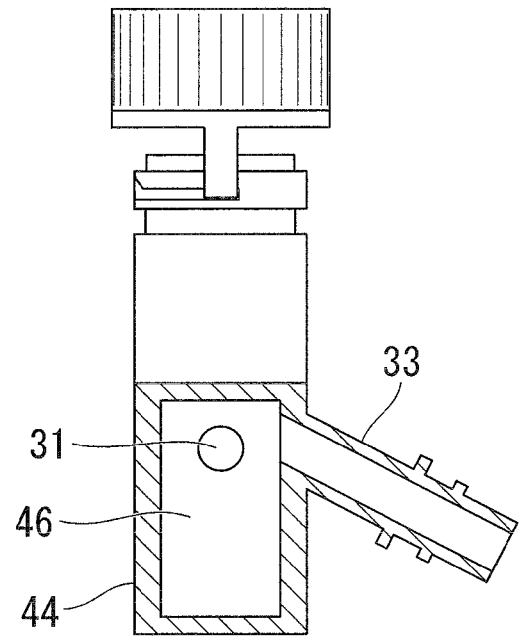
FIG. 17 is a cross-sectional view taken along the line Z-Z in FIG. 14.

FIG. 14 is a perspective view showing a tissue-collecting case 42 of an endoscope system according to the present embodiment. FIGS. 15 to 17 are cross-sectional views taken along the line X-X, the line Y-Y, and the line Z-Z shown in FIG. 14 respectively.

As shown in FIGS. 14 and 15, the tissue-collecting case 42 has a first main body 43, and a casing main unit 60 formed by a second main body 44 connected to the first main body 43. A first chamber 45 is a space defined by an opening section 43A and a bottom section 43B in the first main body 43. A second chamber 46 is a space defined by a ceiling section 44A and a bottom section 44B in the second main body 44.

The bottom section 43B of the first chamber 45 is disposed above the bottom section 44B of the second chamber 46. The first chamber 45 communicates with the second chamber 46 via the communication path 31 having an opening at a lateral wall of each chamber.

The present embodiment has the same functions as those of the aforementioned first embodiment.

Figure 18:
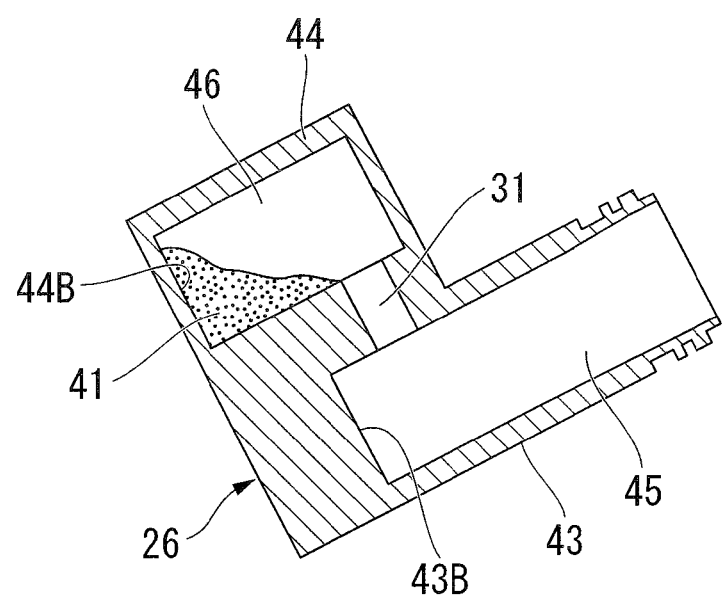
FIG. 18 shows a casing main unit of the tissue-collecting case in a tilted state.

The present embodiment causes the fluid 41 to not be fully suctioned with the incised tissue and remain in the second chamber 46 to resist moving to the first chamber 45 more significantly since the bottom section 44B of the second chamber 46 is formed lower than the bottom section 43B of the first chamber 45. The aspirator 4 is stopped upon seizing the incised tissue by the tissue-collecting filter 25, and then, the tissue-collecting filter 25 is detached from the tissue-collecting case 42 for taking out the seized tissue. Tilting the operation section 6 while continuing operation of the endoscope 2 in this state hardly causes the fluid 41 remaining in the second chamber 46 of the tissue-collecting case 42 to spill out of the tissue-collecting case 42, thereby providing clean operation to the operator and therearound as shown in FIG. 18.

Third Embodiment

A third embodiment of the present invention will be explained with reference to FIGS. 19 to 20B.

Figure 19:
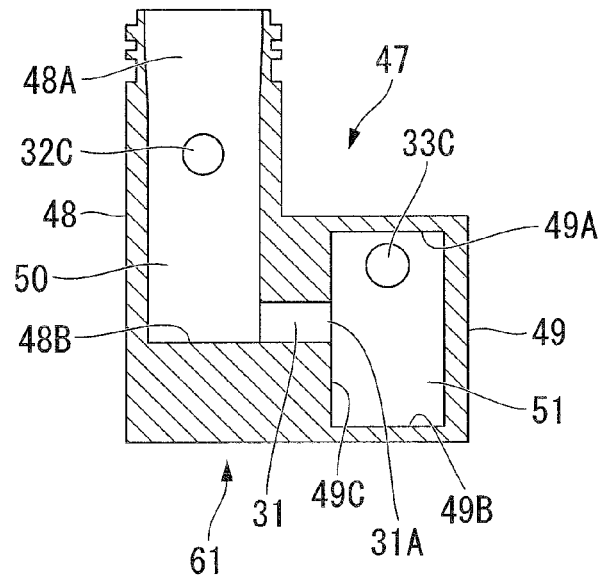
FIG. 19 is a cross-sectional view showing a casing main unit of a tissue-collecting case attached to an endoscope system according to a third embodiment of the present invention.
Figure 20A:
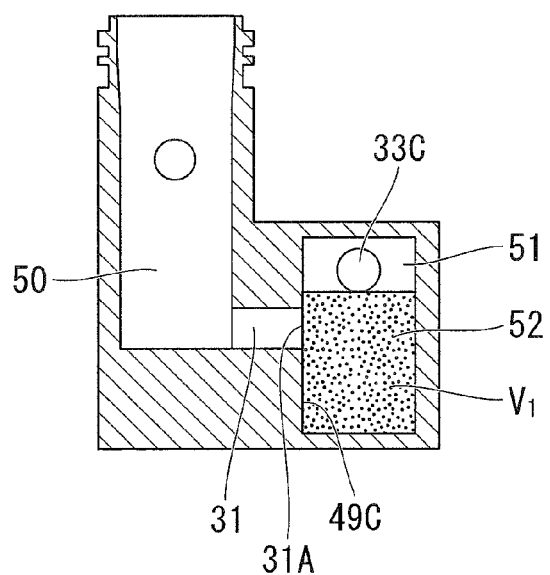
FIG. 20A shows a second chamber of the casing main unit having fluid dwelling thereinside.
Figure 20B:
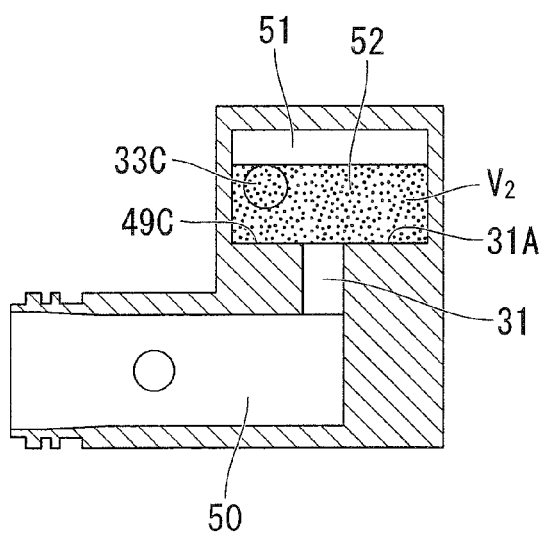
FIG. 20B shows the casing main unit of FIG. 20A in a tilted state.

FIG. 19 is a cross-sectional view showing a casing main unit 61 of a tissue-collecting case 47 attached to an endoscope system according to the present embodiment. As shown in FIG. 19, the casing main unit 61 is formed by a first main body 48 and a second main body 49 connected to the first main body 48. A first chamber 50 is a space defined by an opening section 48A and a bottom section 48B in the first main body 48. A second chamber 51 is a space defined by a ceiling section 49A and a bottom section 49B in the second main body 49. The bottom section 48B of the first chamber 50 is disposed above the bottom section 49B of the second chamber 51. The first chamber 50 communicates with the second chamber 51 via the communication path 31 having an opening end disposed in the vicinity of the bottom section 48B of the first chamber 50 and the other opening end formed to a lateral wall 49C of the second chamber 51. The opening section 31A of the communication path 31 in the second chamber 51 is disposed lower than the second communication port 33C of the proximal end pipeway 33. That is, as shown in FIG. 20A, it is revealed that fluid 52 reaching the lower end of the second communication port 33C of the proximal end pipeway 33 closes the opening section 31A of the second chamber 51 of the communication path 31 fully. Second intra-chamber volume (first volume) V1 obtained with respect to a height from the bottom section 49B to the lower end of the second communication port 33C as shown in FIG. 20A is not smaller than second intra-chamber volume (second volume) V2 obtained based on distance between the bottom section of the lateral wall 49C of the second chamber 51 having the opening of the communication path 31 and the upper end of the second communication port 33C as shown in FIG. 20.

The present embodiment has the same functions as those of the aforementioned first embodiment.

The present embodiment prevents air in the second chamber 51 from moving thereoutside since the opening section 31A of the communication path 31 in the second chamber 51 is disposed at a lower position than that of the second communication port 33C of the proximal end pipeway 33; the second intra-chamber volume V1 obtained with respect to the lower end of the second communication port 33C is not smaller than the second intra-chamber volume V2 obtained based on the distance between the bottom section of the lateral wall 49C having the opening of the communication path 31 and the upper end of the second communication port 33C; the fluid 52 reaching the lower end of the second communication port 33C upon tilting the tissue-collecting case 47 moves in the second chamber 51 while closing the first rotation mechanisms 1351A and 1351B in the second chamber 51; and the second communication port 33C is closed consequently. This results in preventing the fluid 52 remaining in the second chamber 51 from moving to the first chamber 50.

Therefore, the aspirator 4 is stopped upon seizing the incised tissue by the tissue-collecting filter 25, and then, the tissue-collecting filter 25 is detached from the tissue-collecting case 47 for taking out the seized tissue. Tilting the operation section 6 while continuing this state of the endoscope 2 reduces the possibility of the fluid 52 remaining in the second chamber 51 of the tissue-collecting case 47 spilling out of the tissue-collecting case 47, thereby providing clean operation to the operator and therearound.

Fourth Embodiment

A fourth embodiment of the present invention will be explained with reference to FIGS. 21 to 22B.

Figure 21:
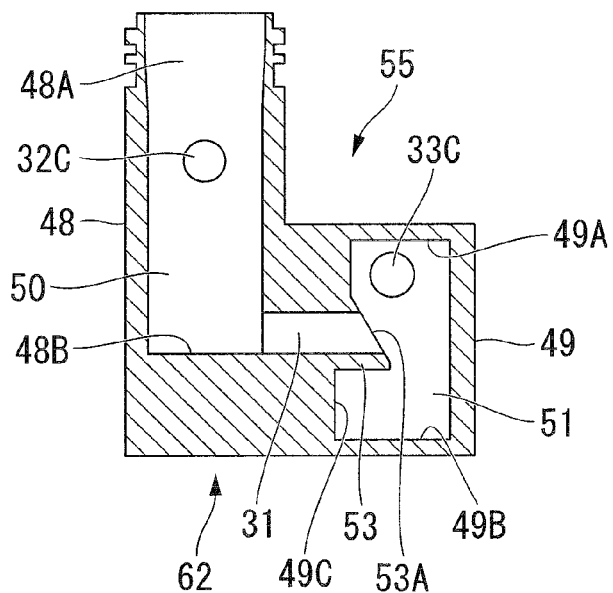
FIG. 21 is a cross-sectional view showing a casing main unit of a tissue-collecting case attached to an endoscope system according to a fourth embodiment of the present invention.
Figure 22A:
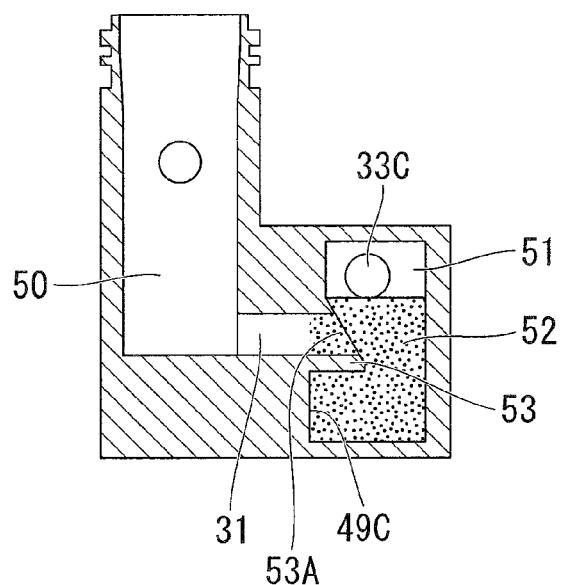
FIG. 22A shows a second chamber of the casing main unit having fluid dwelling thereinside.
Figure 22B:
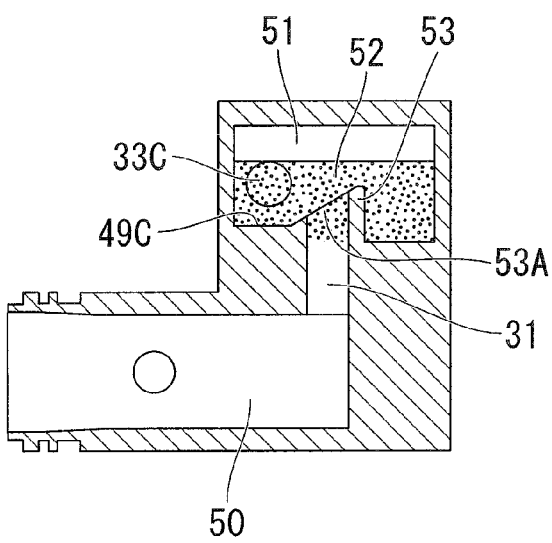
FIG. 22B shows the casing main unit of FIG. 22A in a tilted state.
Figure 23:
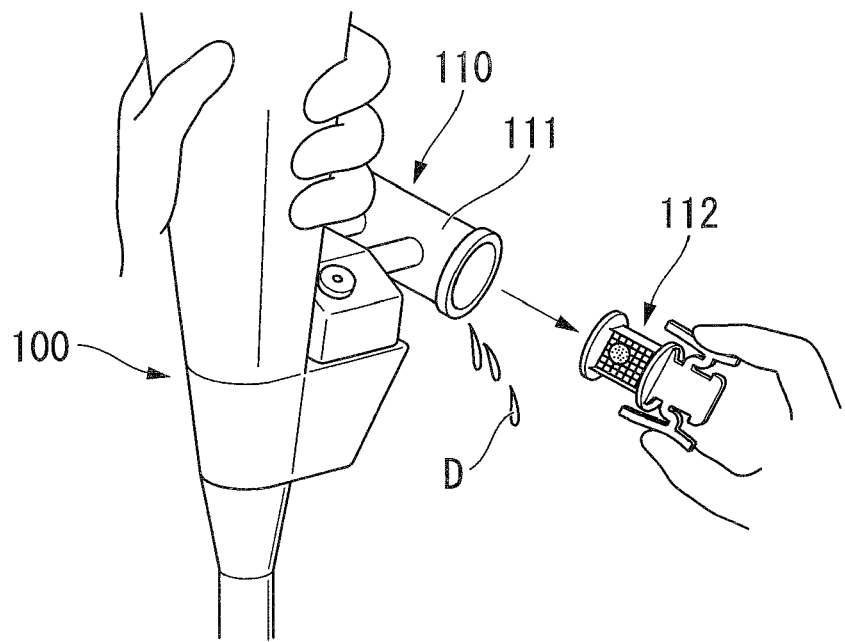
FIG. 23 shows the movement of a conventional endoscope apparatus in use.
Figure 24:
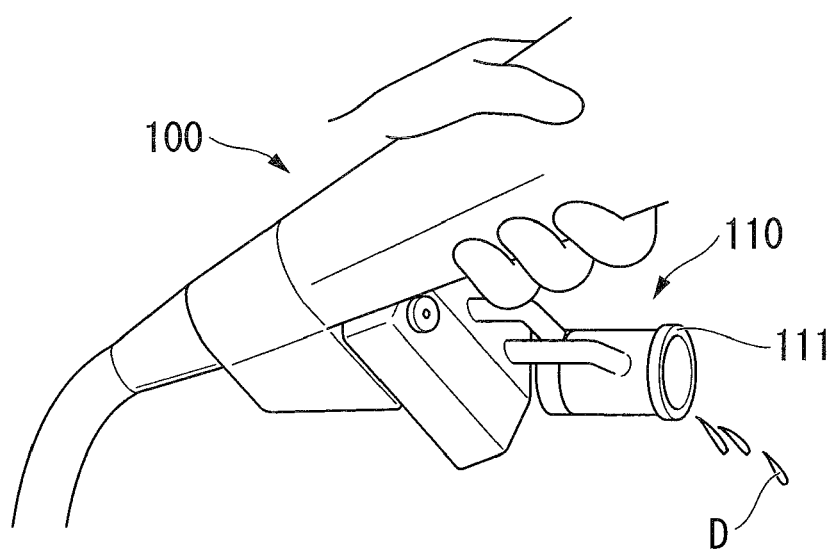
FIG. 24 shows the movement of a conventional endoscope apparatus in use.

FIG. 21 is a cross-sectional view showing a casing main unit 62 of a tissue-collecting case 55 attached to an endoscope system according to the present embodiment. As shown in FIG. 21, a water-level-adjusting section 53 is provided to the lateral wall 49C of the second chamber 51. The water-level-adjusting section 53 is formed to project into the second chamber 51 from the lateral wall 49C so that the second chamber 51 can reduce the volume of itself and so that the communication path 31 extends into the second chamber 51. Providing the water-level-adjusting section 53 causes the value of the first volume V1 and the value of the second volume V2 to be smaller than those of the casing main unit 61 according to the third embodiment. The other structures are the same as those of the casing main unit 61 in the aforementioned third embodiment. The present embodiment has the same functions as those of the aforementioned first embodiment.

The present embodiment prevents the fluid 52 remaining in the second chamber 51 from moving to the first chamber 50 since providing the water-level-adjusting section 53 projecting from the lateral wall 49C of the second chamber 51 causes the water level of the fluid remaining in the second chamber 51 to reach the lower end of the second communication port 33C, thereby closing an opening 53A of the water-level-adjusting section 53 communicating with the communication path 31; the fluid 52 reaching the lower end of the second communication port 33C upon tilting the tissue-collecting case 55 moves in the second chamber 51 and closes the second communication port 33C while closing the opening 53A of the second chamber 51; and air does not move thereoutside. Therefore, the aspirator 4 is stopped upon seizing the incised tissue by the tissue-collecting filter 25, and then, the tissue-collecting filter 25 is detached from the tissue-collecting case 55 for taking out the seized tissue. Tilting the operation section 6 while continuing this state of endoscope 2 hardly causes a small amount of the fluid 52 remaining in the second chamber 51 of the tissue-collecting case 55 to spill out of the tissue-collecting case 55, thereby providing soil-free operation to the operator and therearound.

The present invention is not limited to the above descriptions but is limited only by the appended claims.

What is claimed is:

1. An endoscope system comprising:
an endoscope having an insertion section extending from an operation section operated by an operator into a human body, and an operation channel having a first end section having an opening at a distal end of the insertion section and a second end section passing through the insertion section and having an opening at the operation section;
a tissue-collecting apparatus connected to a connecting pipeway branching from a branch section formed in the vicinity of the second end section in the operation channel, and capable of seizing tissue retracted into the operation channel;
an aspirator for producing suction force for suctioning the tissue into the operation channel; and
a suction pipeway connecting the tissue-collecting apparatus to the aspirator, wherein
the tissue-collecting apparatus has:
a tissue-collecting case having a first chamber connected to the connecting pipeway, a second chamber connected to the suction pipeway, and a communication path provided between a lateral wall of the first chamber and a lateral wall of the second chamber to cause the first chamber to communicate with the second chamber; and
a tissue-collecting filter detachably enclosed in the first chamber,
the first chamber comprises the lateral wall of the first chamber being formed in a cylindrical shape and a bottom section formed in a planar shape, and
a distance between the bottom section of the first chamber and an opening of the communication path which opens in the first chamber is shorter than a distance between a bottom section of the second chamber and an opening of the communication path which opens in the second chamber.

2. The endoscope system according to claim 1, wherein the communication path communicates with an inside of the second chamber at a lower position than the opening of the suction pipeway in the second chamber, and
a first volume of the second chamber obtained based on the height between the bottom section of the second chamber and a lower end of the opening of the suction pipeway is equal to or greater than a second volume of the second chamber obtained based on the height between a bottom section corresponding to a lateral wall of the second chamber having the opening of the communication path thereto and an upper end of the opening of the suction pipeway.

3. The endoscope system according to claim 2, further comprising a water-level-adjusting section having a part of which is disposed to be located in a space defining the second volume.

4. The endoscope system according to claim 1, wherein the communication path is provided such that an axis line of the communication path is perpendicular to an axis line connecting an opening of the connecting pipeway with the bottom section of the first chamber.

* * * * *